US006770674B1

(12) United States Patent
Young

(10) Patent No.: US 6,770,674 B1
(45) Date of Patent: Aug. 3, 2004

(54) MOLLUSC REPELLENT

(76) Inventor: Colin Leslie Young, 27 Reynolds Road, Wattle Glen, Victoria, 3096 (AU)

( * ) Notice: Subject to any disclaimer, the term of this patent is extended or adjusted under 35 U.S.C. 154(b) by 0 days.

(21) Appl. No.: 09/762,585

(22) PCT Filed: Aug. 11, 1999

(86) PCT No.: PCT/AU99/00651

§ 371 (c)(1),
(2), (4) Date: Feb. 9, 2001

(87) PCT Pub. No.: WO00/08933

PCT Pub. Date: Feb. 24, 2000

(30) Foreign Application Priority Data

Aug. 11, 1998 (AU) .............................................. PP 5183

(51) Int. Cl.[7] ........................ A01N 55/02; A01N 55/04; A01N 55/06; A01N 37/04; A01N 65/00
(52) U.S. Cl. ....................... 514/500; 514/492; 514/493; 514/494; 514/495; 514/496; 514/498; 514/499; 514/501; 514/502; 514/503; 514/504; 514/505; 514/574; 514/918; 514/919; 504/100; 504/101; 504/116; 504/187; 504/189; 424/407; 424/195.17; 106/15.05; 106/18.36
(58) Field of Search ................................ 514/492–505, 514/574, 918, 919; 424/407, 195.17; 504/100, 101, 116, 187, 189; 106/15.05, 18.36; 523/122

(56) References Cited

FOREIGN PATENT DOCUMENTS

| AU | 64756/94 | | 12/1994 |
|----|----------|---|---------|
| EP | 485213 | * | 5/1992 |
| WO | 88/00659 | | 8/1988 |
| WO | 92/00550 | | 10/1992 |

OTHER PUBLICATIONS

Chemical Abstracts 123:249144 (1995).*
Chemical abstracts 125:63666 (1996).*
Chemical abstracts 95:186651 (1981).*
Chemical abstracts 91:87852 (1979).*
1996 BCPC Symposium Proceedings No. 66: Slug & Snail Pests in Agriculture: "Metal Chelates as Stomach Poison Molluscicides for Introduced Pests, Helix Aspera, Theba Pisana, Cernuella Virgata and Deroceras Reticulatum in Australia" by C. Young (*Dept. of Chemistry, University of Melbourne, Parkville, Victoria, 3052, Australia*), 1996.

Comprehensive Coordination Chemistry, "The Synthesis, Reactions, Properties & Applications of Coordination Compounds", vol. 2, Ligands, 1987 Pergamon Press, 20.3 (Complexones by Giorgio Anderegg, ETH, Zurich, Switzerland.
1996 BCPC Symposium Proceedings No. 66: Slug & Snail Pests in Agriculture: "Reformulation Studies with Methiocarb" by I.D. Bo wen, S. Antoine and T.J. Martin.
The Journal of Applied Ecology, (1984), vol. 21, 437–443, "Response of Birds to Different Types of Food Repellents" by Michael R. Conover (*Dept. of Ecology and Climatology, The Connecticut Agircultural Experiment Station, P.O. Box 1106, New Haven, Connecticut 06504 U.S.A.*).
"A Dry Non–Phytotoxic Bird and Insect Repellent", vol. 60, 1970, 206, by W.F. Croster, Glenda Nash and D.C. Croster (*Cornell University, Geneva, New York 14456*).
Sax's Dangerous Properties of Industrial Materials, 8th Edition, vol. II, by Richard J. Lewis, SR, date unavailable.
"Solubilization and Transformation of Insoluble Inorganic Metal Compounds to Insoluble Metal Oxalates by *Aspergillus Niger*" by Jacqueline A. Sayer and Geoffrey M. Gadd *Dept. of Biological Sciences, University of Dundee, Dundee, DD1 4HN, U.K.*), 1997.
1996 BCPC Symposium Proceedings No. 66: Slug & Snail Pests in Agriculture: "Physiochemical Barriers as Plaint Protectants Against Slugs (Gastropode:Pulmonata)" by G.W. Dawson, I.F. Henderson, A.P. Martin and B.J. Pye (*IACR–Rothemsted Experimental Station, Harpenden, AL5 2JO, UK*), 1996.
PCT Notification of the International Application No. and of the International Filing Date of International Application No. PCT/AU97/00033, filed Jan. 22, 1997, entitled "Stomach–Action Molluscicides" in the name of Colin Leslie Young, PCT Request and PCT Fee Calculation Sheet together with the specification, received Jan. 31, 1997 by the Patent Cooperation Treaty.

* cited by examiner

*Primary Examiner*—John Pak
(74) *Attorney, Agent, or Firm*—Burns, Doane, Swecker & Mathis, L.L.P.

(57) ABSTRACT

A mollusc repellent, which includes a substantially insoluble metal oxalate and a suitable carrier therefor, which exhibits prolonged efficacy. The mollusc repellent is environmentally friendly, being both non-phytotoxic and harmless to non-target animals, and is therefore suitable for use in sustainable agriculture, where the use of toxic chemicals is unacceptable. The mollusc repellent can be used in the form of a solid or as a coating composition.

39 Claims, No Drawings

MOLLUSC REPELLENT

This application is a 371 of PCT/AU99/00651, filed on Aug. 11, 1999.

FIELD OF THE INVENTION

The present invention relates to a repellent for molluscs. More particularly, the present invention relates to a mollusc repellent, which is environmentally friendly being both non-phytotoxic and harmless to non-target animals, and therefore suitable for use in sustainable agriculture, where the use of toxic chemicals is unacceptable.

BACKGROUND OF THE INVENTION

Slugs and snails are major pests of agriculture in many parts of the world. One particular species of slug, the grey field slug, Deroceras reticulatum, is a common horticultural and agricultural pest in Australia, which causes extensive damage to agricultural crops and garden plants.

Significant crop damage by slugs and snails also occurs in the United Kingdom, Northern Europe, the Middle East, North and Central America, South East Asia, Japan and New Zealand. In many cases, the rise to pest status of the slug in question is a consequence of change—either in distribution (as in the case of accidental or deliberate introductions) or in agricultural practice.

In the recent past, fields awaiting seed planting were subjected to a thorough ploughing which actually resulted in the destruction of slug populations submerged beneath the surface of the soil. This maximum tillage of the soil, though, was found to destroy many beneficial characteristics of the soil structure. More recently, in order to reduce expenditure involved in such thorough ploughing and to overcome the difficulties associated with ploughing in muddy, boggy soils, the practice of minimum tillage and the use of drill holes has increasingly been adopted prior to seed planting. The advent of minimum tillage has contributed significantly to the level of slug populations rising to pest status.

Slugs are a major agricultural pest causing significant crop damage because they bury themselves in the soil and then move into the drill holes into which new crop seeds have been planted. Once the seed has been placed in the drill holes, the slugs attack the seed and eat the inside essentially leaving an empty husk, thereby potentially destroying the whole planting. There is therefore an urgent need for a method of protecting seeds from destruction by slugs prior to the seeds being planted.

There are several other instances where a solution to deal with slug populations is required. For example, in order to control weeds and reduce moisture loss by evaporation, it has been common practice to employ sheets of black polythene laid on the ground around the plants and under organic mulching material. The problem associated with such sheets is that they have to be dug up to dispose of them, they are unsightly and they do not allow passage of water through them. Clearly, the use of such material, which is non-biodegradable, is environmentally unacceptable.

One solution to this problem, which is the subject of Australian Patent No. AU-B-64756/94, has been to employ recycled newspaper waste by reconstituting it into matting, in the form commonly known as "weed mats." Such matting is environmentally friendly since it employs a recycled resource which naturally decomposes. The problem encountered in the use of such matting, however, is that the recycled paper mat is attacked by slugs present in the soil upon which the matting is laid. This attack reduces the effective lifespan of the matting thereby making such a slug barrier unattractive to consumers. In addition, the laying of such matting is very labour-intensive and time-consuming and it would be preferable if the time interval between successive applications could be extended as much as possible. None of the molluscicides presently available on the market are suitable for this application since their efficacy reduces rapidly on contact with water and so would be ineffective in extending the lifespan of the weed mats.

Another case where slugs present a problem is in the agricultural practice of growing brussel sprouts. These crops present one of the few instances where slugs actually move up onto the plant and shelter in the plant itself, rather than stay in the soil and attack the root system. The problem presented in this case is that a slug repellent is required which is non-phytotoxic as well as being harmless to human beings, the eventual consumers of the crop. A further problem is that the slug repellent cannot be in the form of a pellet, but rather in the form of a spray since the repellent has to coat the leaves of the plant. Preferably, the slugs must be prevented from climbing up onto the plants at a very early stage because once they have done so, it has previously been found to be very difficult to remove them. It has been proposed that growers confronted with this problem may use a surfactant repellent such as CeTAB, cetyl tertiary ammonium bromide. However, the efficacy of this repellent is short-lived, since the compound is soluble and washes off in the rain or during overhead irrigation.

As was also mentioned above, one of the ways in which mollusc populations can achieve pest status is that they can be accidentally introduced. One such mode of accidental introduction is where molluscs attach themselves onto the hulls of ships which move from port to port. One way in which such accidental introductions could be prevented is for a mollusc repellent to be applied to the ship's hull thereby preventing the initial harbouring of the mollusc. In the United States, a considerable problem has been encountered in the control of the introduced Zebra mussal, which attaches itself to the inlet and outlet pipes of cooling systems for industrial power generators. This mollusc has now reached plague proportions. To solve the mollusc problems encountered in these two aquatic situations, care has to be taken to apply a mollusc repellent that is not soluble and does not endanger aquatic life. None of the known mollusc repellents would be useful in this application all being either too soluble or too toxic.

Chemical methods (i.e. the use of molluscicides), involving the use of stomach poisons for the control of these pests, are well known. Molluscicides containing metaldehyde and methiocarb have been in use for some time, but these are themselves toxic to non-target animals and human beings and in the form of pellets, they also deteriorate upon exposure to water and in particular, rain and are not sufficiently durable as long-term repellents.

The use of metal complexes in molluscicides was first disclosed in Australian Patent AU-B-22526/88 entitled: "Aluminium(III) and Iron(III) complexes exhibiting molluscicidal activity", in the name of Henderson et al. In one of their studies, these inventors compared the relative toxicities of some aluminium and iron salts and chelates and their efficacies as stomach poisons by injecting known amounts into the gut lumen of molluscs and they found that the metal chelates were more toxic than their corresponding salts. Metal chelates were also first trialed by Henderson et al as contact-action poisons. In one particular study, Henderson used the metal chelate, FeEDTA, as the toxic agent, finding it just as effective as various salts of Fe(III). (Henderson, I. F. et al, in "A New Group of Molluscicidal Compounds," BCPC mono., (1989), 41, "Slugs and Snails in World Agriculture", pp 289–294 eds. Henderson, I. F., British Protection Council, Farnham, U.K.). More recently, Australian Patent No. 683405 entitled: "Ingestible Mollusc Poisons," disclosed a terrestrial mollusc stomach poison containing as the active ingredient either ferric edetate or the ferric hydroxy-ethyl derivative of edetic acid. These workers have also shown that mixtures of iron salts such as ferric sulphate, ferric chloride or ferric nitrate when mixed together with disodium EDTA or EDTA, as such, are toxic to the slug species, Deroceras reticulatum. The present inventor has also developed a stomach-action molluscicide, disclosed in Australian Patent Application No: 689399, containing the oxodimer, [EDTA-Fe-O-Fe-EDTA]4- as the active ingredient wherein the bait formulation itself was found to be more palatable to molluscs and therefore also more efficacious. While metal chelate-derived molluscicides are preferable to the use of the more toxic alternatives, such molluscicides are all soluble and are therefore not applicable to any of the problems outlined above.

Dawson et al, in BCPC Symposium Proceedings, (1996), 66, "Slug & Snail Pests in Agriculture," p 439–444, eds. Henderson, I. F., British Protection Council, Farnham, U.K.) have investigated the repellency of a range of surfactants to the slug, Deroceras reticulatum. They found that in particular, tetraammonium salts were highly repellent and some polyphenylpolyethoxylates were also repellent with the degree of repellency varying with the degree of ethoxylation. These workers were interested in using surfactants as a repellent to crops. Their laboratory tests showed that crawling slugs rapidly detect and are deterred by topical applications of chemicals at low deposit rates. They concluded however, that surfactants were of limited use in this type of application, since they were rapidly removed from the plant by rain, by condensation or by irrigation spraying.

Mollusc repellent formulations commonly in use contain methibcarb, copper sulphate, aluminium sulphate, ammonium alum and thiram to mention a few. Aluminium sulphate and ammonium alum work as taste repellents, whilst methiocarb and thiram are toxic poisons. Copper sulphate and copper oxychloride have been used for some time as slug repellents but they are too soluble to be effective as a slug repellent for the above-mentioned application to seeds and moreover both have a low LD50 value (see Table 1) by virtue of them being soluble and therefore being able to enter the blood stream by biochemical degradation. In addition, they are both phytotoxic. Copper silicate, which is the subject of Australian Patent Application No. AU-B-27621/92, is also believed to function as a fungicide and a pesticide. Although this compound is not phytotoxic, it is too soluble to be able to function effectively as the active ingredient in a durable mollusc repellent composition for a seed coating or for any of the applications mentioned above.

Accordingly, it is an object of the present invention to provide a mollusc repellent which achieves the hitherto unavailable requirement of prolonged repellency. It is also an object of the present invention to provide a mollusc repellent, which is environmentally friendly being both non-phytotoxic and harmless to non-target animals, and therefore suitable for use in sustainable agriculture, where the use of toxic chemicals is unacceptable.

The present study concentrated on finding an active ingredient, for both horticultural and agricultural purposes, which acted both as a repellent to molluscs and one that remained efficacious in field conditions on prolonged exposure to the environment. To this extent, the study was also directed to finding a mollusc repellent that was effective in both marine and fresh-water environments. The results of trials conducted on several metal complexes revealed that some metal oxalates, and copper oxalate, in particular, when applied in either humid or moist environments, showed a surprisingly propensity to remain efficacious for a prolonged period of time.

In addition, the acute toxicity of copper oxalate is not known, but it is estimated that the toxicity is low (i.e. greater than 1000 mg/kg of body weight). This estimation is based on the following reasoning. Copper oxalate has extremely low solubility in water over a considerable range of pH. It is thought that only a minuscule amount of copper oxalate will be absorbed in the mammalian gut. The toxicity of a range of copper compounds is known and these are summarised in Table 1. It is apparent that compounds with low solubility are not very toxic. Oxalates are known to be toxic and some data are given in Table I. Oxalates occur in a wide range of natural products including some foods, such as tea, wheat, spinach and rhubarb. Actual poisoning by oxalate is known to arise more from natural sources than from synthetic materials. It appears that the toxicity of oxalates is due to the fact that they chelate metals that are needed for biochemical/metabolic processes.

Copper oxalate itself occurs naturally in the soil due to the decomposition of organic matter. The fact that copper oxalate is very insoluble seems to be employed by certain common soil fungi, Aspergillus niger, which has been found to solubilize a number of minerals including cuprite, $CuO_2$ with no reduction in growth rate. (Sayer, J. A., Kierans, M. and Gadd, G. M., "Solubilisation of some Naturally Occurring Metal-bearing Minerals, Limescale and Lead Phosphate by Aspergillus niger," FEMS Microbiology Letters, (1997), 154, 29–35, published by Elsevier). After one to two day's growth on cuprite at 25° C., a precipitate of copper oxalate was observed. It was suggested that this oxalate formation represented a reduction in bioavailability of toxic cations and represented an important means of toxic metal immobilisation of physiological and environmental significance. A certain amount of copper is, of course essential for both plant and animal life, it being an important co-enzyme in a number of biochemical reactions. The average daily requirement for man is estimated to be 2–5 mg per day (Henry Osiecki, "Nutrients in Profile," (1995), published by Bioconcepts Pty Ltd).

SUMMARY OF THE INVENTION

According to one aspect of the present invention, there is provided a mollusc repellent composition including an effective amount of a substantially insoluble metal oxalate and a suitable carrier therefor.

Preferably, the metal of the metal oxalate is selected from a transition metal or a transition metal in combination with a non-transition metal. More preferably, the metal is selected from the group of iron(II) or iron(III), aluminium, zinc or copper. Most preferably, the metal is copper. Preferably, the non-transition metal is potassium. Preferably, the metal oxalate is selected from ferric potassium oxalate or copper oxalate. Most preferably, the metal oxalate is copper oxalate.

Typically, the amount of metal oxalate required for efficacy is between about 2% and 100% by weight of the total composition of the repellent. Preferably, the amount of metal oxalate is between about 2% and 10% by weight of the total composition. Most preferably, the amount is about 5% by weight of the total composition.

Preferably, the carrier of the composition is water, such that the metal oxalate forms an aqueous suspension. Preferably, the carrier comprises between about 0% and 98% by weight of the total composition.

Typically, the repellent composition is applied to an article from which it is desired to repel molluscs. Preferably, the article includes animate and inanimate articles. More preferably, the animate article is selected from seeds, including wheat, barley, grass (clover, phalaris, rye and cocksfoot), canola seeds, fruit or vegetables. More preferably, the inanimate article is selected from weed mats, inlet and outlet pipes for cooling systems, hulls of ships and other sub-aqueous structures, driveways or parking aprons of homes and grow-bags, but is not limited to these.

The mollusc repellent is advantageously presented in a solid form, such as tablets, powders, granules, as a suspension or as a coating composition. Preferably, the coating composition is in the form of a paint. Those skilled in the art will appreciate that it is preferable to prepare the products, which are the subject of the invention, in a form that is easy for consumers to use.

In a preferred form of the invention, the carrier of the composition includes a binder, which facilitates the adhesion of the metal oxalate onto the surface of the article to be treated. Preferably, where the repellent composition is to be applied to an animate article, the binder is selected from gum arabic or gum acacia. Preferably, where the repellent is to be applied to inanimate articles, the binder is selected from a waterproof binder such as paraffin wax, white oil, casein or polyvinylacetate. Preferably, the binder comprises between about 0.1% and 100% by weight of the carrier of the composition. More preferably, the binder comprises 0.5% to 3% by weight of the carrier.

Preferably, the composition further includes a fungicide such that the article is protected from attack by a fungus. Preferably, the fungicide is selected from copper oxychloride or thiram. Preferably, the fungicide comprises about 0.05% to 1.0% by weight of the total composition.

Typically, the fungicide is applied as a coating in combination with a small amount of a non-phytotoxic dye, the latter being used as an indicator that the seeds have been treated with a fungicide. Preferably, the non-phytotoxic dye comprises less than about 1% by weight of the total composition.

Preferably, the carrier further comprises a diluent to ensure even coverage of the article to which the repellent is to be applied. Preferably, the diluent is selected from a silicate, gypsum or limestone. Preferably, the diluent comprises between about 0% to 95% by weight of the carrier.

According to yet another aspect of the invention, the composition comprises a metal oxalate in combination with at least one other mollusc repellent.

Preferably, where the treated article is a seed having the potential to produce at least one root, the composition further includes a growth hormone such that the hormone is readily available to the at least one root as it emerges from the seed. Preferably, the growth hormone is a seaweed extract. Preferably, the growth hormone comprises between about 0.05% and 1% by weight of the total composition.

In another preferred embodiment, the repellent composition is in the form of a paint, wherein the carrier is preferably selected from an aqueous surfactant solution, an aqueous polyvinylacetate solution or an oil-based paint.

The mollusc repellent may also conveniently be presented as a two-part composition, wherein the first part comprises an effective amount of an aqueous solution of oxalic acid or soluble metal oxalate and the second part comprises an effective amount of an aqueous solution of a soluble metal salt, whereby sequential application of the two solutions, in either order, results in the in-situ preparation of a substantially insoluble metal oxalate as an aqueous suspension. Preferably, the metal oxalate is selected from ferrous oxalate, ferric ammonium/potassium oxalate or copper oxalate. Preferably, the oxalic acid and the metal salt are present in equimolar amounts. Preferably further, the concentration of the metal salt solution is about 5% by weight of the total two-part composition. Such use of two environmentally acceptable chemicals renders such a mollusc repellent suitable for sustainable agriculture purposes.

According to another aspect of the invention, there is provided a method of treating an article with the mollusc repellent, which is the subject of the invention, including applying the composition to the surface of the article to be treated. Tablets, powders or granules can be sprinkled over the ground or in places where molluscs congregate, such as letterboxes, to repel the molluscs. An aqueous suspension of metal oxalate composition as detailed above can be used for coating seeds, for spraying on driveways, for spraying on the trunks of fruit trees or on vegetable seedlings, such as brussel sprouts. A repellent composition can be applied either in the solid form, by sprinkling on the surface of, or in the form of a coating composition by coating on the surface of, the lining of grow-bags, used by the home gardener, or on at least one of the layers that comprise "weed mats", as described above. A repellent composition in the form of a paint, can be applied to sub-aqueous surfaces which are potentially susceptible to mollusc colonies forming thereon, such as inlet and outlet pipes for cooling systems or on the hulls of ships, to prevent the introduction of foreign species of unwanted molluscs from other parts of the world.

According to another aspect of the invention, the invention provides an article, which has been treated with the mollusc repellent composition. Preferably, the treated article is selected from a seed, a weed mat, a citrus tree, a driveway, a sub-aqueous structure such as an inlet or outlet pipe or a ship's hull, a growbag, a vegetable seedling, but is not limited to one of these.

The scope of the present invention also extends to the use of the mollusc repellent composition by, for example, spreading the repellent composition in a solid form as tablets, granules or as a powder; by coating animate or inanimate articles with the composition, for example, by spraying vegetable seedlings or driveways with an aqueous suspension of the repellent composition; by applying a paint including the composition to subaqueous inlet or outlet pipes, ships' hulls or any other sub-aqueous structure where molluscs are likely to congregate; or by coating layers of decomposable material incorporated into weed mats with the composition. These examples for the use of the composition are by no means limiting.

EXAMPLES

The oral toxicity of several soluble copper compounds and oxalates which have been extracted from "SAX'S Dangerous Properties of Industrial Materials," edited by Lewis, R. J., are given in Table 1. LD50 values have generally been given for the rat since these were available for all the chemicals of interest in this study. However, where available, LD50 values for human beings have also been given.

TABLE 1

Oral Toxicity of several soluble copper compounds and oxalates

| Chemical Compound | LD50 (Rat) mg/kg | LD50 (Human) mg/kg |
|---|---|---|
| Copper acetate | 595 | |
| Copper oxychloride | 700 | |
| Copper citrate | 1580 | |
| Copper nitrate | 940 | |
| Copper sulphate | 300 | 50 |
| Copper hydroxide | | 200 |
| Oxalic acid | 7500 | |
| Potassium oxalate | 660 | |

The results in Table 1 show that several copper compounds have by shown quite considerable toxicity to the rat and to the human being, whereas because copper oxalate is insoluble, its LD50 values both for the rat and the human being would be expected to be large.

The invention will now be illustrated with reference to the following non-limiting Examples.

Example 1

There are many possible variables to consider when evaluating mollusc repellents. Field trials are often poorly controlled and it is often difficult to arrive at unambiguous conclusions. It is impossible to apply extensive statistical analysis to poorly designed or controlled experiments. However, a series of simple experiments in which variables are controlled lead to unambiguous conclusions with no need for statistical analysis. It was decided to compare the repellents under laboratory conditions, which could closely mimic controlled field conditions.

Repellency of the test compounds was tested using the sectorised filter technique of Bowen and Antoine (see Bowen, I. D. and Antoine, S., "Molluscicide Formulation Studies," International Journal of Pest Management, (1995), 41(2), 74–78.)

The compounds tested were copper oxalate and CeTAB (cetyl tertiary ammonium bromide). One sector of the filter paper was used as the control and this was moistened with distilled water (1 ml). The other half was moistened with the test compound. The copper oxalate used in the trial was insoluble and so was rubbed into the filter paper and the weight of the solid held on the filter paper was calculated. The paper containing the copper oxalate was moistened with water after the addition of the chemical.

Filter sectors were placed on the lid of a plastic tub. The tub was inverted and was used to make a closed test arena. A small gap of 2 mm was left between the two filter sectors so as to prevent mixing of the test paper with the control. One juvenile Helix aspersa was introduced to the control sector and was allowed to remain in the arena overnight.

Attractancy/repellency was detected by dusting the filter paper with charcoal to reveal the slug trails. The results were quantified by placing a transparent grid over the test sectors and measuring the area covered by snail trails. Any phago-stimulatory effect of the test compound was indicated by the consumption of the treated paper.

Results

The results of the arena trials including the final position of each snail at the end of the experiment, the percentage of the filter paper section eaten and the percentage trail cover are shown in Table 2.

TABLE 2

Results of attractancy/repellency tests on Copper oxalate and CeTAB

| Treatment | Concentration (mg/cm2) | Final Position | % Sector Eaten Test | % Sector Eaten Control | % Covered Test | % Covered Control |
|---|---|---|---|---|---|---|
| Control | | C | 5 | 3 | 84 | 88 |
| | | C | 5 | 1 | 88 | 80 |
| | | T | 0 | 5 | 88 | 77 |
| CeTAB | 0.2 | R | 0 | 2 | 20 | 86.7 |
| | 0.2 | R | 0 | 4 | 22 | 77.8 |
| | 0.2 | R | 0 | 1 | 42.2 | 75.6 |
| | 2.0 | R | 0 | 4 | 0 | 62.2 |
| | 2.0 | R | 0 | 5 | 0 | 66.6 |
| | 2.0 | R | 0 | 3 | 0 | 71.1 |
| Copper oxalate | 2.11 | R | 0 | 5 | 0 | 71.1 |
| | 1.61 | R | 0 | 4 | 4.4 | 88 |
| | 2.43 | R | 0 | 2 | 0 | 68.9 |
| | 2.47 | R | 0 | 5 | 0 | 86.7 |
| | 3.46 | R | 0 | 1 | 4.4 | 66.7 |
| | 3.19 | C | 0 | 2 | 0 | 88 | where R: roof of the container; T = test sector; and C = control sector.

Summary of Results

The results show that snails were strongly repelled by the copper oxalate. In all, of the six snails tested, none were found in the test sector at the end of the experiment and there was no consumption of the test filter paper. There was very little mucous cover compared to the control. The positive control, CeTAB, was also found to act as a repellent. Indeed, there was a concentration-related response, more snails being repelled by 2.0 mg/l CeTAB, compared to 0.2 mg/l CeTAB.

Example 2

In the following experiment, various seeds were coated with copper oxalate and ferric potassium oxalate, respectively and fed to the slug, Deroceras reticulatum. The damage to these seeds was compared to damage to control seeds, which were left untreated. The percentage of seeds that were damaged was calculated and is given in Table 3.

TABLE 3

Protection afforded to seeds by Copper oxalate and Ferric potassium oxalate

| Treatment | % Seeds damaged Wheat seeds After 5 days | % Seeds damaged Wheat seeds After 7 days | % Seeds damaged Pea seeds After 5 days | % Seeds damaged Pea seeds After 7 days | % Seeds damaged Broad beans After 7 days |
|---|---|---|---|---|---|
| Control | 37 | 87 | 15 | 33 | 5 |
| Copper oxalate | 0 | 2 | 7 | 7 | 5 |
| Ferric potassium oxalate | 3 | 20 | 15 | 17 | 0 |

Summary of Results

It can be seen from the above results that copper oxalate is a very effective slug repellent for wheat and pea seeds.

Example 3

In the following experiment, the efficacy of copper oxalate for the protection of seeds was tested and compared to BAYSOL® and MULTIGUARD®. The results are shown in Table 4. Seeds were coated with an aqueous suspension of copper oxalate, dried and fed to the slug, Deroceras reticulatum.

TABLE 4

Protection afforded to wheat and pea seeds by copper oxalate compared to BAYSOL ® and MULTIGUARD ®

| Treatment | % Seeds damaged Wheat seeds After 9 days | % Seeds damaged Pea seeds After 7 days |
| --- | --- | --- |
| Control | 72 | 23 |
| Copper oxalate | 10 | 8 |
| MULTIGUARD ® |  | 2 |
| BAYSOL ® | 10 | 4 |

MULTIGUARD ® and BAYSOL ® are registered trade marks of Multicrop ® (Aust.) Pty Ltrd and Bayer, respectively.

Summary of Results

The above results show that copper oxalate dramatically reduces the amount of damage to wheat seeds and does so to the same extent as BAYSOL®, a toxic molluscicide containing methiocarb Copper oxalate was also found to be effective at protecting pea seeds from damage by slugs although not as effectively as MULTIGUARD® which was more effective then BAYSOL®. These latter two products also resulted in the death of the slugs involved in the trial.

Example 4

In the following experiment, the repellency of copper oxalate was investigated when incorporated in a paint composition. In this example, the carrier used was a common aqueous PVA solution sold in Australia under the brand name of Bond Crete.

Thirty-three 1 liter containers were used each with 3 layers of paper towel covering the bottom of the container. Half of the uppermost surface of each of the paper towels was coated with a solution made from 1 part copper oxalate: 10 parts water: 1 part PVA emulsion. This coating was applied at a rate of about 2 ml per 100 cm2 and allowed to dry. The towel was then moistened with approximately 20 ml of water. One snail, Cernuella virgata, was placed in the centre of the paper towels at the border of the coated and the uncoated half in each container. The snails were observed to move away from the coated area or move along the border without moving on to the coated area. Some of the snails were observed to move away from the bottom of the container at night, but most returned to the moist paper towel in the morning. The snails consumed some of the untreated paper. No consumption of the treated paper was detected. After 7 days, the number of snails on the treated and untreated sections of the paper towel were counted, together with the number on the sides and lid of the container. The results are shown in Table 5.

TABLE 5

Investigation of the repellency of copper oxalate in a coating composition

| Area where snail located in container | No. of snails in area |
| --- | --- |
| On lid of container | 1 |
| On side of container | 1 |
| On Treated half of paper | 8 |
| On untreated half of paper | 23 |

Summary of Results

These results show that when incorporated into a coating composition, copper oxalate functions effectively as a mollusc repellent Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification (unless specifically excluded) individually or collectively, and any and all combinations of any two or more of said steps or features.

Where the terms "comprise", "comprises", "comprised" or "comprising" are used in this specification, they are to be interpreted as specifying the presence of the stated features, integers, steps or components referred to, but not to preclude the presence or addition of one or more other feature, integer, step, component or group thereof.

What is claimed is:

1. A method for treating an article with a mollusc repellent composition which method comprises applying to the surface of said article, a mollusc repellant composition comprising an effective amount of a substantially insoluble metal oxalate and a suitable carrier therefor, wherein the article is above ground or in the soil, and wherein the mollusc is *Deroceras spp., Helix spp.*, or *Cerneuella spp.*

2. The method of claim 1, wherein the metal of the metal oxalate is a transition metal or a transition metal in combination with a non-transition metal.

3. The method of claim 1, wherein the metal is iron(II) or iron(III), aluminum, zinc or copper.

4. The method of claim 1, wherein the metal oxalate is ferric potassium oxalate or copper oxalate.

5. The method of claim 1, wherein the amount of metal oxalate is between 2% to 100% by weight of the total composition.

6. The method of claim 5, wherein the amount of metal oxalate is between 2% to 10% by weight of the total composition.

7. The method of claim 1, wherein the metal oxalate is present as an aqueous suspension.

8. The method of claim 1, wherein the carrier comprises a binder to facilitate the adhesion of the metal oxalate onto the surface of an article to be treated.

9. The method of claim 8, wherein the binder comprises between 0.1% and 100% by weight of the carrier.

10. The method of claim 1, wherein the mollusc repellent composition further comprises a fungicide.

11. The method of claim 10, wherein the fungicide comprises about 0.05% to 1.0% by weight of the total composition.

12. The method of claim 1, wherein the composition further comprises a diluent to enable even coverage of the article to which the repellent is to be applied.

13. The method of claim 12, wherein the diluent comprises between about 0% to 95% by weight of the total composition.

14. The method of claim 1, wherein the composition further comprises a growth hormone.

15. The method of claim 14, wherein the growth hormone is a seaweed extract.

16. The method of claim 14, wherein the growth hormone comprises between 0.05% and 1% by weight of the total composition.

17. The method of claim 1, wherein the composition comprises said metal oxalate in combination with at least one other mollusc repellent.

18. The method of claim 1, wherein the article to be treated is an animate or an inanimate article.

19. The method of claim 2, wherein the animate article is a seed having the potential to produce at least one root, and a growth hormone is readily available to the at least one root as it emerges from the seed.

20. The method of claim 18, wherein the inanimate article is a weed mat, an outlet pipe for cooling systems, a hull of a ship, a driveway of a home, or a grow-bag.

21. The method of claim 1, wherein the form of the repellent is a solid, a suspension, or a coating composition.

22. A mollusc repellent composition comprising an effective amount of a substantially insoluble metal oxalate, a suitable carer therefor, and a growth hormone.

23. The mollusc repellent composition of claim 22, wherein the metal of the metal oxalate is a transition metal or a transition metal in combination with a non-transition metal.

24. The mollusc repellent composition of claim 22, wherein the metal is iron(II) or iron(III), aluminum, zinc or copper.

25. The mollusc repellent composition of claim 22, wherein the metal oxalate is ferric potassium oxalate or copper oxalate.

26. The mollusc repellent composition of claim 22, wherein the amount of metal oxalate is between 2% to 100% by weight of the total composition.

27. The mollusc repellent composition of claim 26, wherein the amount of metal oxalate is between 2% to 10% by weight of the total composition.

28. The mollusc repellent composition of claim 22, wherein the metal oxalate is present as an aqueous suspension.

29. The mollusc repellent composition of claim 22, wherein the carrier comprises a binder to facilitate the adhesion of the metal oxalate onto the surface of an article to be treated.

30. The mollusc repellent composition of claim 29, wherein the binder comprises between 0.1% and 100% by weight of the carrier.

31. The mollusc repellent composition of claim 22, further comprising a fungicide.

32. The mollusc repellent composition of claim 31, wherein the fungicide comprises about 0.05% to 1.0% by weight of the total composition.

33. The mollusc repellent composition of claim 22, wherein the composition further comprises a diluent to enable even coverage of the article to which the repellent is to be applied.

34. The mollusc repellent composition of claim 33, wherein the diluent comprises between about 0% to 95% by weight of the total composition.

35. The mollusc repellent composition of claim 22, wherein the growth hormone is a seaweed extract.

36. The mollusc repellent composition of claim 22, wherein the growth hormone comprises between 0.05% and 1% by weight of the total composition.

37. The mollusc repellent composition of claim 22, wherein the composition comprises a metal oxalate in combination with at least one other mollusc repellent.

38. The mollusc repellent composition of claim 22, wherein said composition is in the form of coating composition.

39. The mollusc repellent composition of claim 22, wherein said composition is in the form of a paint.

* * * * *